US 6,652,566 B2

(12) United States Patent
Larnard et al.

(10) Patent No.: US 6,652,566 B2
(45) Date of Patent: *Nov. 25, 2003

(54) NEUROSURGICAL DEVICE FOR THERMAL THERAPY INCLUDING SPIRAL ELEMENT

(75) Inventors: Donald J. Larnard, Hampton Falls, NH (US); Dan Sachs, Boston, MA (US)

(73) Assignee: Seacoast Technologies, Inc., Portsmouth, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/971,073

(22) Filed: Oct. 4, 2001

(65) Prior Publication Data

US 2002/0123783 A1 Sep. 5, 2002

Related U.S. Application Data

(60) Provisional application No. 60/238,314, filed on Oct. 5, 2000.

(51) Int. Cl.[7] .................................................. A71F 7/12
(52) U.S. Cl. .................. 607/105; 607/112; 607/113
(58) Field of Search ............................ 607/105, 110, 607/112, 113, 96, 104

(56) References Cited

U.S. PATENT DOCUMENTS

| 3,170,465 A | 2/1965 | Henney et al. ............. 128/401 |
| 3,220,414 A | 11/1965 | Johnston ..................... 128/400 |
| 3,504,674 A | 4/1970 | Swenson et al. ......... 128/303.1 |
| 3,736,936 A | 6/1973 | Basiulis et al. .......... 128/303.1 |
| 3,776,241 A | 12/1973 | Magilton et al. ........... 128/400 |
| 3,897,790 A | 8/1975 | Magilton et al. ........... 128/400 |
| 4,010,795 A | 3/1977 | Stenberg |
| 4,207,897 A | 6/1980 | Lloyd et al. ............. 128/303.1 |
| 4,719,919 A | 1/1988 | Marchosky et al. ........ 128/401 |
| 4,781,193 A | 11/1988 | Pagden ....................... 128/402 |

(List continued on next page.)

FOREIGN PATENT DOCUMENTS

| EP | 0586567 | 3/1994 |
| RU | 211736 | 11/1968 |
| RU | 293381 | 12/1971 |
| RU | 432907 | 6/1974 |
| RU | 639557 | 12/1978 |
| RU | 833266 | 5/1981 |
| RU | 1138152 | 2/1985 |
| RU | 1544422 | 2/1990 |
| RU | 1745238 | 7/1992 |
| RU | 1787026 | 1/1993 |
| RU | 2100989 | 1/1998 |

OTHER PUBLICATIONS

Perov, et al., "Design of Thermodes for Cooling Sites of Cerebral Hemisphere Cortex in Chronic Tests", Sechenov Physiology Journal of the USSR, No. 7, 1983, Methods of Physiological Investigations, 5 pgs.

Mursky, "On the Use of Complex (Cranial Cerebral and General) Hypothermia in Experiments", Brain Hypothermia, 1965, 4 pgs.

Shilo, et al., "Delivery/Dialysis Cannula for Local Superfusion of Brain Structures at Cranial Cerebral Hypothermia", Collection of Scientific Works, 1988, 3 pgs.

Rybakov, "Method of Intra–Ventricle Hypothermia of Brain", 3 pgs.

Primary Examiner—Linda C. M. Dvorak
Assistant Examiner—Henry M. Johnson, III
(74) Attorney, Agent, or Firm—Christopher & Weisberg, P.A.

(57) ABSTRACT

A device for thermally affecting tissue having a thermally transmissive contact member being in thermal communication with a thermal member and a surface area expansion element configured for contacting a tissue. The contact member and thermal member are disposed within a housing and the surface area expansion element is coupleable to the housing. The housing is configured to fit within an opening in a skull.

17 Claims, 4 Drawing Sheets

U.S. PATENT DOCUMENTS

| | | | |
|---|---|---|---|
| 4,860,744 A | 8/1989 | Johnson et al. | 128/303.1 |
| 4,946,460 A | 8/1990 | Merry et al. | 606/24 |
| 4,989,601 A | 2/1991 | Marchosky et al. | 128/399 |
| 5,108,407 A | 4/1992 | Geremia et al. | |
| 5,207,674 A * | 5/1993 | Hamilton | 606/20 |
| 5,209,227 A * | 5/1993 | Deutsch | 607/104 |
| 5,261,399 A | 11/1993 | Klatz et al. | 607/104 |
| 5,304,214 A | 4/1994 | DeFord et al. | 607/105 |
| 5,334,181 A | 8/1994 | Rubinsky et al. | 606/22 |
| 5,380,319 A | 1/1995 | Saito et al. | 606/28 |
| 5,417,686 A | 5/1995 | Peterson et al. | 606/25 |
| 5,474,533 A | 12/1995 | Ward et al. | 604/26 |
| 5,520,682 A | 5/1996 | Baust et al. | 606/24 |
| 5,531,776 A | 7/1996 | Ward et al. | 607/105 |
| 5,540,711 A | 7/1996 | Kieturakis et al. | 606/192 |
| 5,549,559 A | 8/1996 | Eshel | 604/113 |
| 5,591,162 A | 1/1997 | Fletcher et al. | 606/25 |
| 5,607,443 A | 3/1997 | Kieturakis et al. | 606/192 |
| 5,609,620 A | 3/1997 | Daily | |
| 5,611,767 A | 3/1997 | Williams | 600/2 |
| 5,624,392 A | 4/1997 | Saab | 604/43 |
| 5,643,207 A | 7/1997 | Rise | 604/93 |
| 5,645,528 A | 7/1997 | Thome | 604/96 |
| 5,713,923 A | 2/1998 | Ward et al. | 607/3 |
| 5,716,353 A | 2/1998 | Matsuura et al. | 606/22 |
| 5,716,386 A | 2/1998 | Ward et al. | 607/106 |
| 5,718,584 A | 2/1998 | Wong | 433/168.1 |
| 5,718,684 A | 2/1998 | Gupta | 604/96 |
| 5,730,756 A | 3/1998 | Kieturakis et al. | 606/190 |
| 5,772,680 A | 6/1998 | Kieturakis et al. | 606/190 |
| 5,814,014 A | 9/1998 | Elsberry et al. | 604/43 |
| 5,817,123 A | 10/1998 | Kieturakis et al. | 606/192 |
| 5,843,075 A | 12/1998 | Taylor | 606/34 |
| 5,871,498 A | 2/1999 | Jervis et al. | 606/192 |
| 5,891,134 A | 4/1999 | Goble et al. | |
| 5,899,898 A | 5/1999 | Arless et al. | 606/22 |
| 5,913,885 A | 6/1999 | Klatz et al. | 607/104 |
| 5,916,212 A | 6/1999 | Baust et al. | 606/22 |
| 5,916,242 A | 6/1999 | Schwartz | 607/113 |
| 5,928,203 A | 7/1999 | Davey et al. | 604/247 |
| 5,951,512 A | 9/1999 | Dalton | 604/93 |
| 5,957,963 A | 9/1999 | Dobak, III | 607/104 |
| 5,976,109 A | 11/1999 | Heruth | 604/140 |
| 6,004,337 A | 12/1999 | Kieturakis et al. | 606/190 |
| 6,015,382 A | 1/2000 | Zwart et al. | 600/207 |
| 6,015,421 A | 1/2000 | Echeverry et al. | 606/190 |
| 6,017,324 A | 1/2000 | Tu et al. | 604/96 |
| 6,030,412 A | 2/2000 | Klatz et al. | 607/104 |
| 6,042,579 A | 3/2000 | Elsberry et al. | 604/891.1 |
| 6,045,532 A | 4/2000 | Eggers et al. | 604/114 |
| 6,051,019 A | 4/2000 | Dobak, III | 607/104 |
| 6,053,913 A | 4/2000 | Tu et al. | 606/41 |
| 6,073,051 A | 6/2000 | Sharkey et al. | 607/99 |
| 6,074,412 A | 6/2000 | Mikus et al. | 607/105 |
| 6,083,148 A | 7/2000 | Williams | 600/2 |
| 6,090,132 A | 7/2000 | Fox | 607/96 |
| 6,096,068 A | 8/2000 | Dobak, III et al. | 607/105 |
| 6,106,518 A | 8/2000 | Wittenberger et al. | 606/23 |
| 6,113,593 A | 9/2000 | Tu et al. | 606/34 |
| 6,117,128 A | 9/2000 | Gregory | 606/7 |
| 6,122,549 A | 9/2000 | Sharkey et al. | 607/99 |
| 6,123,718 A | 9/2000 | Tu et al. | 607/113 |
| 6,126,680 A | 10/2000 | Wass | 607/96 |
| 6,126,684 A | 10/2000 | Gobin et al. | 607/113 |
| 6,129,736 A | 10/2000 | Jervis et al. | 606/192 |
| 6,132,415 A | 10/2000 | Finch et al. | 604/502 |
| 6,146,411 A | 11/2000 | Noda et al. | 607/105 |
| 6,149,677 A | 11/2000 | Dobak, III | 607/106 |
| 6,152,920 A | 11/2000 | Thompson et al. | 606/41 |
| 6,156,057 A | 12/2000 | Fox | 607/96 |
| 6,168,608 B1 | 1/2001 | Echeverry et al. | 606/190 |
| 6,179,831 B1 | 1/2001 | Bliweis | 606/21 |
| 6,183,501 B1 | 2/2001 | Latham | 607/109 |
| 6,248,126 B1 | 6/2001 | Lesser et al. | 607/113 |
| 6,277,143 B1 * | 8/2001 | Klatz et al. | 607/104 |
| 6,322,559 B1 | 11/2001 | Daulton et al. | |
| 6,383,210 B1 | 5/2002 | Magers et al. | |
| 6,427,089 B1 * | 7/2002 | Knowlton | 607/101 |
| 2002/0077682 A1 * | 6/2002 | Lee et al. | 607/113 |

* cited by examiner

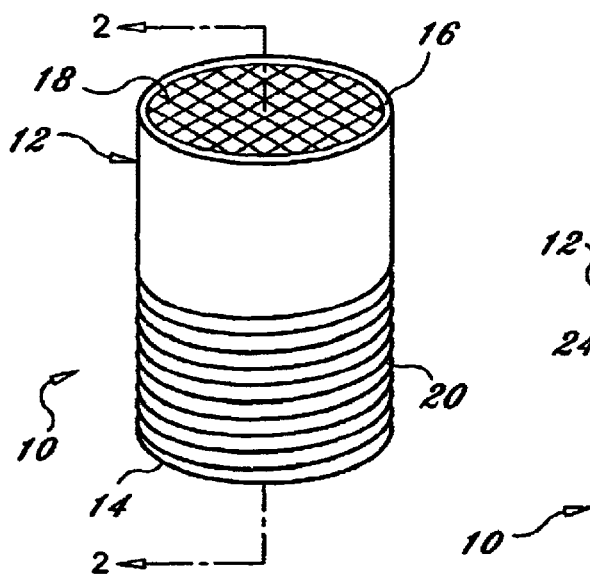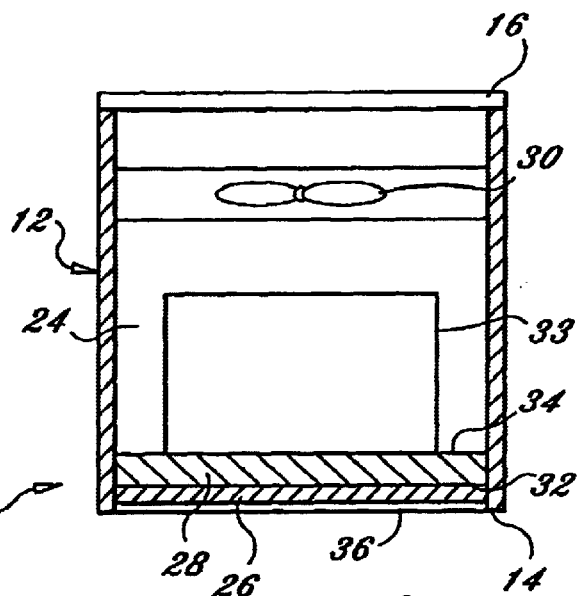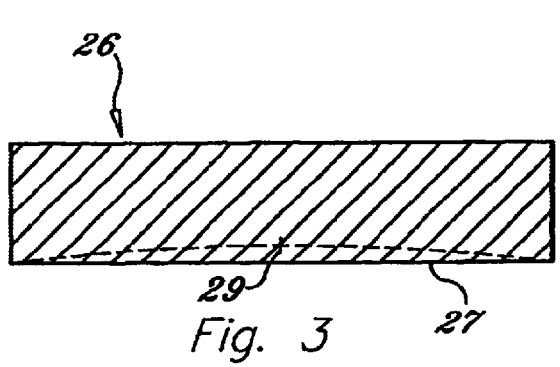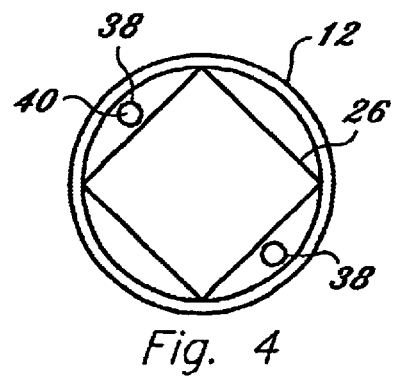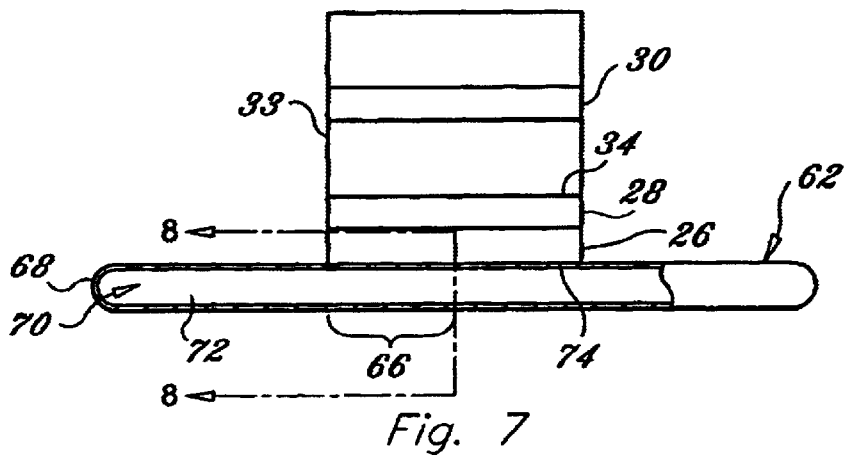

NEUROSURGICAL DEVICE FOR THERMAL THERAPY INCLUDING SPIRAL ELEMENT

CROSS-REFERENCE TO RELATED APPLICATION

This application is related to and claims priority to U.S. Provisional Patent Application Serial No. 60/238,314, filed Oct. 5, 2000, entitled Systems and Methods for Controlling Temperature of Brain Tissue, the entirety of which is incorporated herein by reference.

STATEMENT REGARDING FEDERALLY SPONSORED RESEARCH OR DEVELOPMENT n/a

FIELD OF THE INVENTION

The present invention relates to systems and methods for controlling brain tissue temperature, and in particular to systems and methods for subcranial temperature control of brain tissue through the use of contact cooling devices.

BACKGROUND OF THE INVENTION

Researchers and physicians have long recognized the consequences of reduction of body temperature in mammals, including induction of stupor, tissue damage, and death. Application of freezing and near freezing temperatures to selected tissue is commonly employed to preserve tissue and cell (e.g. sperm banks); and application of extreme cold (far below freezing) is effective for tissue ablation. However, localized cooling (not freezing) of tissue has generally been limited to the placement of an "ice-pack" or a "cold compress" on injured or inflamed tissue to reduce swelling and the pain associated therewith. Localized cooling of internal organs, such as the brain, has remained in large part unexplored.

For example, "brain cooling" has been induced by cooling the blood supply to the brain for certain therapies. However, as the effects of the cool blood cannot be easily localized, there is a systemic temperature reduction throughout the body that can lead to cardiac arrhythmia, immune suppression and coagulopathies.

Attempts have been made to localize cooling of the brain with wholly external devices, such as cooling helmets or neck collars. However, there are disadvantages associated with external cooling to affect internal tissue. For example, external methods do not provide adequate resolution for selective tissue cooling, and some of the same disadvantages that are associated with systemic cooling can occur when using external cooling devices.

It is therefore desirable to obtain improved devices and methods that allow for localized brain cooling without the disadvantages of the known systemic and external devices and techniques.

SUMMARY OF THE INVENTION

The present invention overcomes the disadvantages of known systemic and external devices and techniques by providing localized brain cooling with a device placed through the skull.

The present invention provides a device and method for localized temperature control of a body part, such as the brain. In an exemplary embodiment, a device for thermally affecting tissue of a patient includes a housing defining an interior volume that is at least partially insertable into an exterior opening in a patient, such as a burr hole though the skull. A thermal member positioned within the interior volume of the housing includes a thermal input side and a thermal output side to impart a thermal change to the tissue. An exemplary method of treatment using the device includes the steps of exposing tissue to be thermally affected; attaching a thermal device to an anchor point of the body; positioning the thermal member near or on the tissue; and operating the thermal member to thermally change the temperature of the tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 is a perspective view of an exemplary embodiment of a device constructed in accordance with the principles of the present invention;

FIG. 2 is a section view taken along section 2—2 of FIG. 1;

FIG. 3 is a side view of a base of the device;

FIG. 4 illustrates a contact member on the bottom of the device of FIG. 1;

FIG. 7 is a section view taken along section 7—7 of the device shown in FIG. 6;

DETAILED DESCRIPTION OF THE INVENTION

Figure 5:
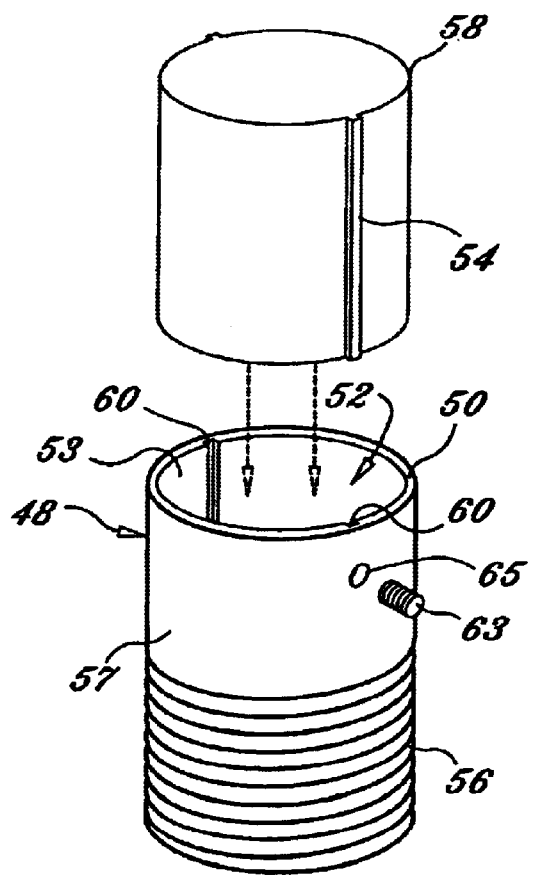
FIG. 5 is an exploded view of another embodiment of a device constructed in accordance with the principles of the invention.

The present invention provides a device for applying thermal energy to a localized region of a body tissue. Referring now to the drawing figures in which like reference designators refer to like elements, there is shown FIG. 1 a perspective view of an exemplary embodiment of a device constructed in accordance with the principles of the present invention and designated generally as device 10. The device 10 includes a housing 12 with a first end 14, a second end 16 and an optional circulation vent 18 through which a thermally conductive fluid can pass. The housing 12 can be constructed of any suitable material, for example metals, plastics or a combination thereof. It is contemplated that the housing 12 has a diameter "D", measured at the widest portion of the device, from approximately one centimeter to approximately ten centimeters. In an exemplary embodiments the diameter ranges from approximately 1 centimeters to 1.5 centimeters. Optional radial threads 20 are provided on the exterior of the housing 12 to facilitate attachment to bone structure such as a skull. However, it is contemplated that non-threaded arrangements can also be provided or coupled to or on the housing 12, for example, flutes, barbs, ridges or other anchoring elements. The term fluid as used herein refers to a substance in a liquid state, a gaseous state, a transition state between liquid and gas, or a combination of any of the preceding.

FIG. 2 is a sectional view of the device of FIG. 1, taken along line 2—2. The housing 12 is a generally cylindrical body having a wall that defines an interior space 24. Provided within the interior space 24, starting at the first end 14 and moving to the second end 16, is a contact member 26 which can be configured to directly contact a tissue or to contact an intermediate material. The contact member 26 can be constructed of any thermally conductive material, for example, stainless steel, aluminum, copper, titanium, various polymers or other such materials. Additionally, adjacent the contact member 26 is a thermal member 28. The thermal member 28 has a thermal input side 32 in thermal communication with the contact member 26 and a thermal output side 34. The thermal member 28 can be a thermoelectric cooler as is known in the art, for example, a peltier cooler. Optionally, a thermal dissipation member 33 is provided in thermal communication with the output side 32 of the thermal member 28. Such devices are known in the art, for example a common thermal dissipation member is a heat sink. However, many alternate components for dissipating thermal energy can be provided. Further, it is contemplated that fewer elements can be provided, for example the thermal member 28 can be configured to act as a thermal contact member without the aid of a separate element.

Further provided within the housing 12 in the interior space 24 is a fluid circulation member 30. The term "fluid" as used herein generally refers to any flowable substance, including but not limited to gasses and liquids. An exemplary fluid circulation member 30 is a cooling fan. The fluid circulation member 30 is positioned such that it circulates a fluid, such as air, across the thermal output side 32 of the thermal member 28 or the optional thermal dissipation member 33 if provided, thereby removing thermal energy dissipated by the thermal member 28. Alternatively, it is contemplated that a pump, used in association with a thermally conductive liquid, be provided to dissipate thermal energy generated by the output side 32 of the thermal member 28. In addition, an optional membrane 36 is provided in thermal communication with the contact member 26. Membrane 36 can be constructed of any bio-compatible material and can be constructed to directly contact a tissue.

Referring to FIG. 2, the operation of an exemplary device is now discussed in detail. Power is supplied to the thermal member 28 through electrical wires (not shown) which in turn creates a thermal input side 32 and a thermal output side 34 to the thermal member 28 (the thermal member discussed here is a peltier cooler and its function is well known in the art). By operation of the thermal member 28, the thermal input side 32 has a reduced temperature relative to the thermal output side 34 which causes a cooling effect at the thermal input side 32. The thermal input side 32 being in thermally conductive contact with the contact member 26, thereby causes a reduction of the relative temperature of the contact member 26. The output side 34 being in thermally conductive contact with the optional thermal dissipation member 33 thereby raises the relative temperature of the thermal dissipation member 33 (creating heat). Additionally, a current or activation energy is supplied to the fluid circulation member 30 to thereby circulate air through the thermal dissipation member 33 and out of housing 12 through the circulation vent 18. Heat dissipated by the thermal dissipation member 33 is removed and discharged from the housing 12 to maintain a reduced temperature at the contact member 26. As such, the concepts of the present invention provide a device 10 for localized cooling of a tissue in a compact configuration.

FIG. 3 is a side view of the contact member 26 showing a contact side 27 having a concave surface as illustrated in phantom. The extent of curvature can modified to accommodate the requirements of the therapy and the tissue site to be treated. The depth of the cavity formed by the concave surface can be measured from the contact side 27 perpendicular to the center 29 of the concave region. In exemplary embodiments the concave distance ranges from approximately 0.001 inches to approximately 0.05 inches. In the embodiment shown in FIG. 3, which is used to treat dura matter, the concave distance is approximately 0.02 inches.

FIG. 4 illustrates the first end 14 of the device 10, wherein a square-shaped contact member 26 is disposed within the housing 12. Optionally, one or more access ports 38 are provided through the housing 12 to allow passage or placement of devices such as specialty neuro-catheters, thermocouple probes, temperature sensors, and pressure sensors. Alternatively, an insert 40 can be provided to be completely or partially obstruct the access port 38. The insert 40 can be constructed from any suitable material, for example, rubber, silicone, aluminum or other such materials. While FIG. 4 shows a square-shaped contact member 26, it is contemplated that various other shapes can be provided. Additionally, an access port (not shown) can be provided through the contact member 26 itself to accommodate accessory devices as discussed above.

FIG. 5 is an exploded view of another configuration for the device, wherein a housing 48 has a wall 50 that defines an inner volume 52 to receive a thermal cartridge 58. The housing includes longitudinal grooves 54 on the inner surface 53 of the wall 50. Radial threads 56 can be provided for securing the housing 48 to the skull. The thermal cartridge 58 has axial slots 60 configured to be slidably engagable with axial grooves 54 of the housing 48.

The thermal cartridge 58 includes the exemplary elements as discussed above for applying thermal energy to a tissue site, for example, a contact member, a thermal member, and a cooling fan (not shown). In practice, the housing 48 is secured within a skull opening by screwing the radial threads into the bone. The thermal cartridge 58 is then inserted into the inner volume 50 of the housing 48 while aligning the axial slots 60 with the axial grooves 52. The thermal cartridge 58 can be slidably adjusted within the insert housing 48 in order to specifically locate the contact member against the dura matter.

Additionally, the thermal cartridge 58 can be moved in response to dura swelling or shrinkage that may occur during treatment. Once a desired distance of insertion is reached, the thermal cartridge 58 is held in position by a set screw 63 through a screw opening 65 in the insert housing 48. While FIG. 7 illustrates an axial groove and slot arrangement, it is contemplated that alternate configurations can be provided. For example, a spiral groove and slot arrangement can be provided which would provide insertion depth adjustment via rotation of the thermal cartridge relative to the housing.

Figure 6:
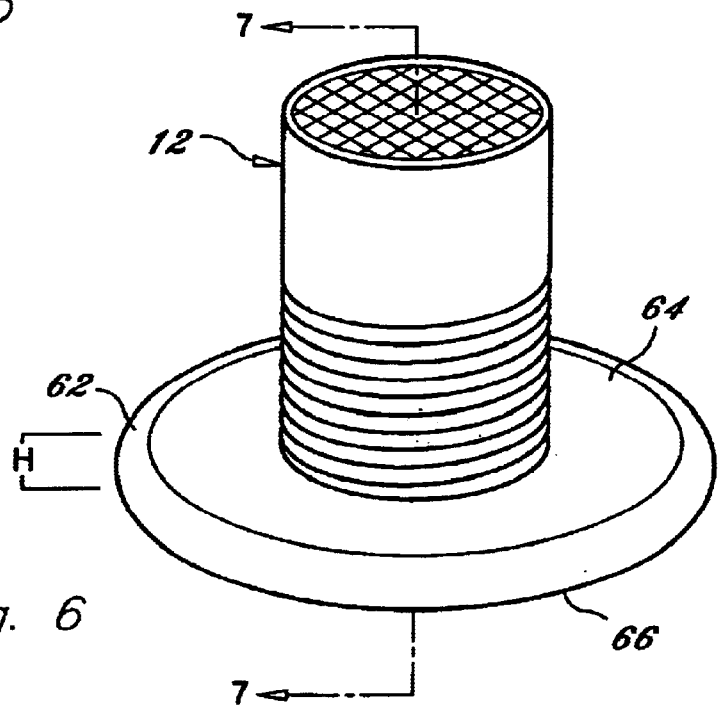
FIG. 6 is a perspective view of yet another device constructed in accordance with the principles of the invention.

FIG. 6 is a perspective view of another feature of the invention, wherein a surface area expansion element 62 is disposed at the first end 14 of the housing 12. The surface area expansion element 62 provides a tissue contact area that is larger than the contact member 26 (not shown). The surface area expansion element 62 has a height "H" measured from a top 64 to a tissue contact area 66 of the surface area expansion element 62 and a deployed diameter "$d_d$" measured from the widest points at a periphery of the surface area expansion element 62. In an exemplary embodiment, the surface area expansion element 62 has a height to width ratio of approximately one to two. Further, a surface area expansion element 62 constructed in accordance the principles of the present invention can have a deployed diameter dd ranging in size from 5 to 200 mm. An exemplary embodiment has a deployed diameter 34 of 48 mm. Another exemplary embodiment has a deployed diameter 34 of 64 mm. Further, an exemplary embodiment can have a height H ranging in size from 1 to 10 mm. In one exemplary embodiment the height H is approximately 4 mm.

The surface area expansion element 62 can be provided by several different structures, such as an inflatable plenum such as a bladder or balloon. Alternatively, the expansion element 62 can include foldable, rollable, or compressible, ribbons or resilient thermally-conductive structures. Exemplary resilient materials include rubber, silicon, flexible polymers and other materials known in the art. Thus, the surface area expansion element 62 is provided with a structure that allows it to be inserted through a small opening in a body and then deployed to increase the tissue contact area 66. The tissue contact area 66 can have a shape ranging from substantially flat to concave.

FIG. 7 is a view taken along section 7—7 of the device shown in FIG. 6 to show the hollow interior of the surface area expansion element 62. As illustrated, the surface area expansion element 62 has a wall 68 which defines an interior volume 70 which is filled with a thermally transmissive fluid 72. The contact member 26 is in thermal contact with the interior volume 70 via the thermally transmissive fluid 72 at an interface 74. The contact member 26 is in turn in thermal contact with the thermal member 28. Optionally, a thermal dissipation member 33 can be provided in thermal communication with the output side 34 of the thermal member 28. Further, the fluid circulation member 30 is provided in fluid communication with the thermal dissipation member 33. In practice, the cooling of the contact member 26 in turn cools the thermally transmissive fluid 72. The thermally transmissive fluid cools the tissue contact area 66 which in turn cools the contacted tissue. The surface area expansion element 62 can have other shapes, such as round, oval, oblong, spider-like, or amorphous.

Figure 8:
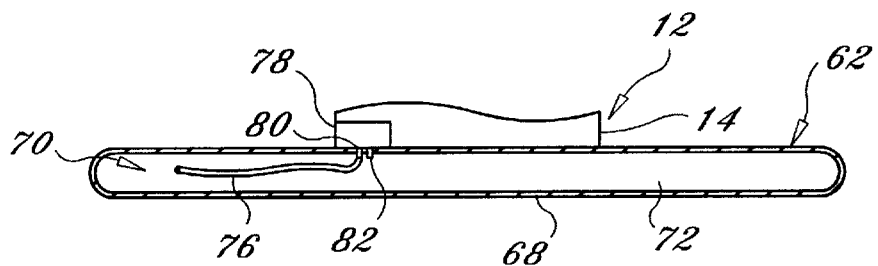
FIG. 8 is a sectional side view taken along section 8—8 of the device of FIG. 7.

FIG. 8 is a sectional view of the expansion element 62 taken along section 8—8 shown in FIG. 7. The expansion element 62 is attached to the first end 14 of the housing 12 and includes a wall 68 that defines an interior volume 70. A hollow injection member 76 having a proximal end and a distal end is disposed within the interior volume 70. A circulation member 78 having an outlet 80 and an inlet 82 is in fluid communication with the proximal end of the injection member 76 via the outlet 80. An example of a circulation member 78 is a fluid pump. An exemplary thermally transmissive fluid 72 is a saline solution. The arrangement of the circulation member 78, outlet 80, injection member 76, inlet 82, and interior volume 70 define a circulation circuit.

In operation, thermally transmissive fluid 72 is provided within the interior volume 70 and is drawn into the circulation member 78 via the inlet 82. The fluid 72 is then directed through the outlet 80, the proximal end of the injection member 76, and the distal end, where it is expelled into the interior volume 70. Alternately, the circulation member 78 can be in thermal contact with the thermal element 28, thereby affecting the temperature of the thermally transmissive fluid directly, or the thermally transmissive fluid can be in direct contact with the contact member 26. It is contemplated that the circulation member 78 can be provided away from and separate from the device. It is further contemplated that such a separate circulation member 78 could reside external to the body to be treated and be in fluid communication with the device via various methods that are known in the art.

Figure 9:
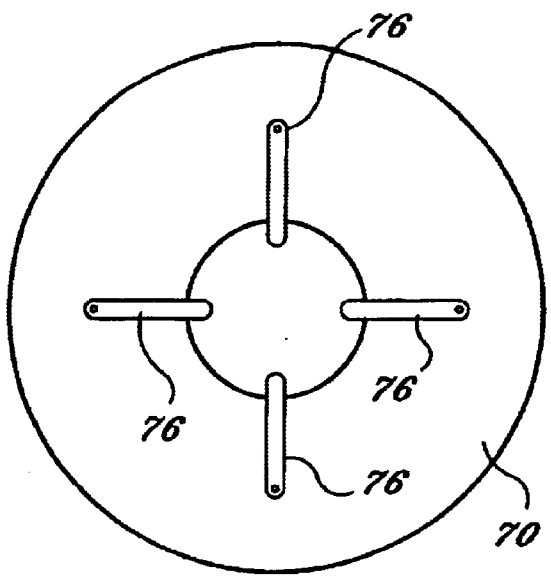
FIG. 9 is a sectional end view of an expansion element of the device shown in FIG. 7.

FIG. 9 is an end view of the device in which several injection members 76 are provided within the interior volume 70 to direct thermally transmissive fluid within the interior volume 70.

Figures 10, 11:
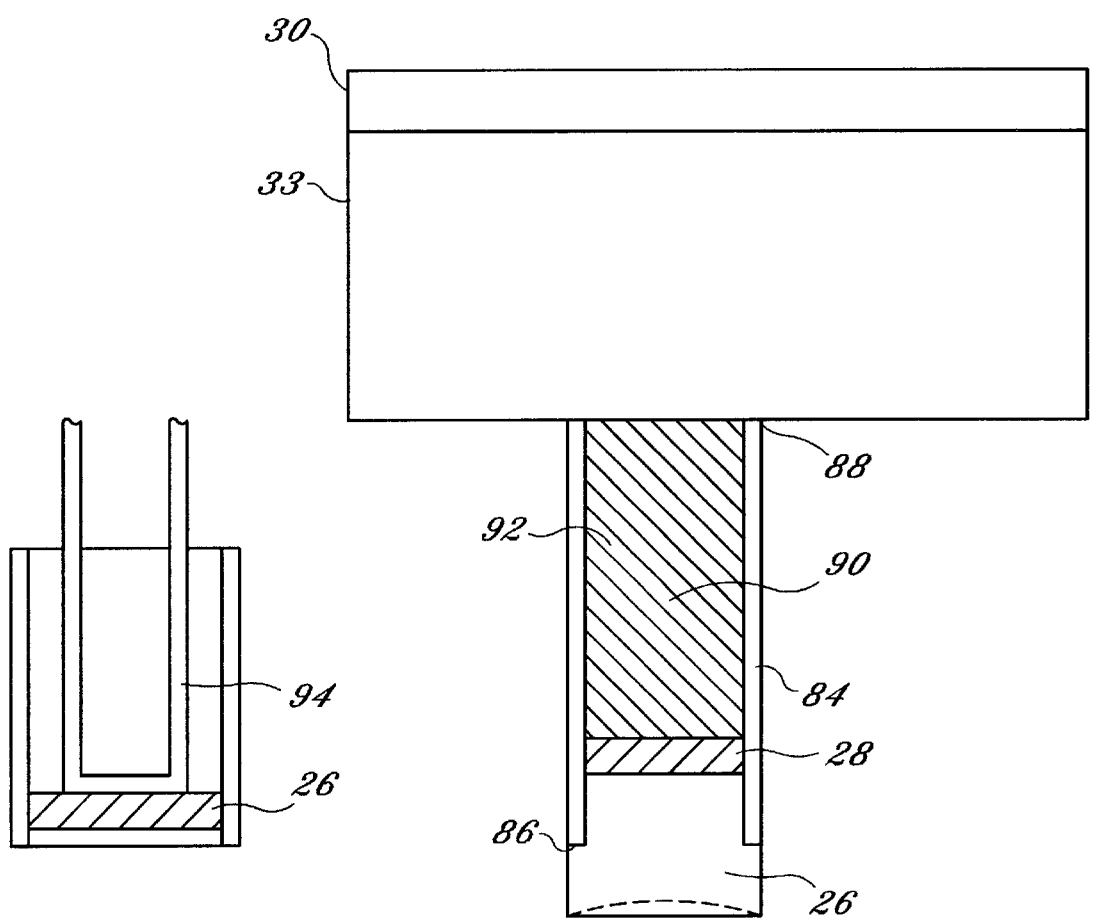
FIG. 10 is a sectional view of an alternative arrangement of a device constructed in accordance with the principles of the present invention.
FIG. 11 illustrates in cross-section yet another arrangement of a device constructed in accordance with the principles of the present invention.

FIG. 10 is a sectional view of an alternate arrangement of the thermal cartridge 58 shown in FIG. 7. In this configuration, the cartridge 58 includes a wall 84, a proximal end 86, and a distal end 88; wherein the wall defines a space 90 to receive a thermal bridge 92, contact member 26, and thermal member 28. The contact member 26 is attached to the proximal end 86 of the cartridge 58. Near the distal end 88 of the cartridge 58, the thermal member 28 is provided within the space 90 adjacent and in thermal communication with the contact member 26. Still further toward the distal end 88, the thermal bridge 92 is in thermal communication with the thermal member 28. Attached to the distal end 88, and in thermal communication with the thermal bridge 92, is a thermal dissipation element 33 which is coupled to a fluid circulation member 30.

The thermal bridge 92 is provided to allow the thermal dissipation member 33 to be distanced from the thermal member 28. In some embodiments it is desirable to have thermal dissipation and fluid circulation members which are larger than the diameter of the housing of the device. By providing a thermal bridge 92, this is possible. While the thermal bridge 92 is described in association with the device shown in FIG. 7, it is contemplated that the thermal bridge 92 and expanded thermal dissipation member 33 can be provided in all of the embodiments of the invention.

FIG. 11 illustrates another cartridge configuration for thermal transfer, wherein a fluid conduit 94 is provided in thermal communication with the thermal output side 34 of a thermal dissipation member 33. In practice, a thermally transmissive fluid is circulated through the fluid conduit 94. When the fluid transits the portion of the fluid conduit that is in thermal communication with the thermal output side 34, thermal energy is dissipated to the fluid which is then circulated to a remote fluid chiller and then re-circulated through the fluid conduit 94.

Figure 12:
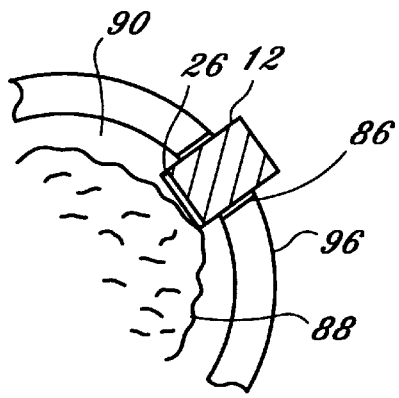
FIG. 12 depicts the exemplary device of FIG. 1 inserted through a skull.

FIG. 12 depicts a device 10, such as shown in FIG. 1, screwed into a burr hole 96 in a skull 98, wherein a contact element 26 is in thermally conductive contact with dura tissue 100 at a location where treatment is desired.

Figure 13:
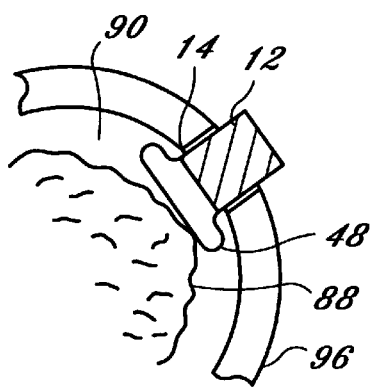
FIG. 13 depicts the exemplary device of FIG. 8 inserted through a skull.

FIG. 13 depicts a device 10, such as shown in FIG. 8, shown screwed into a burr hole in a skull 98. Attached to the first end 14 of the device 10 is a surface area expansion element 62. The surface area expansion element 62 is configured to fit within a space 102 between the dura tissue 100 and the skull 96 without substantially damaging dura tissue 100. For example, in order to fit within the space 102, the surface area expansion element 62 can have a flattened configuration as described in more detail herein. In an alternate embodiment, such a surface area expansion element 62 can be configured to be placed into subdural space within a body to be treated.

The present invention provides a thermocooler based device which is used to impart a thermal change to living tissue. The present invention advantageously provides a user an ability to control the temperature of a localized region of brain tissue. A procedure using the thermocooling device is accomplished by inserting the device into a burr hole in the skull. An exemplary application is to directly contact the brain tissue with the thermocooling device cooling plate in order to lower the localized brain temperature as a neuroprotective measure in a post-stroke condition. Alternatively, the thermocooling device 10 is used to cool localized regions of the brain in a brain trauma patient as a way of lowering cerebral metabolic requirements and minimizing brain edema. Furthermore, the thermocooling device 10 can be used in any post-operative trauma situation when the possibility of cerebral edema exists such that the cerebral edema is desired to be abated or minimized. The above described device can be used in other parts of the body in instances where local tissue temperature needs to be controlled or modulated. In such instances, thermal therapy may involve using either chilled or heated portions of the device to achieve the desired result.

Figure 14:
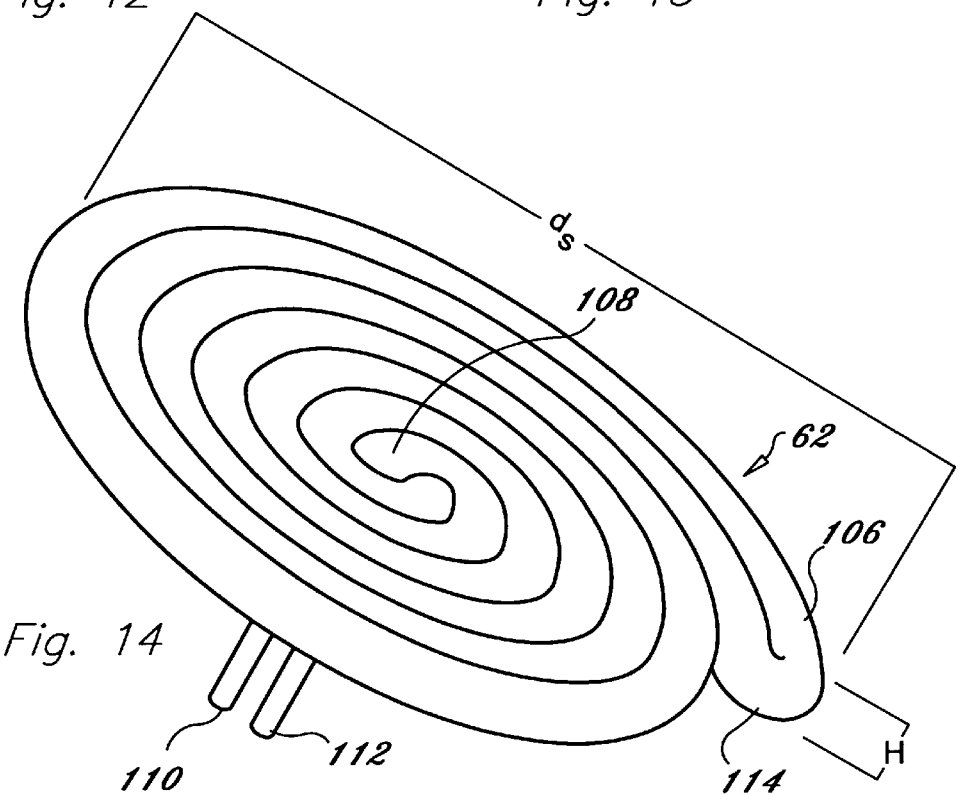
FIG. 14 is a perspective view of an exemplary surface area expansion element.

FIG. 14 is a perspective view of an alternate surface area expansion element 62 as shown in FIGS. 8, 9 and 10. Surface area expansion element 62 has a conduit 106 that defines a spiral shape. The conduit 106 has a proximal end 108 having a fluid inlet 110 and a fluid outlet 112 and a distal end 114. The surface area expansion element 62 is defined by the conduit 106. The coil can be provided by a folded conduit 106 as shown in FIG. 14 or by a singular section of the conduit 106. In operation, a thermally transmissive fluid is supplied to the fluid inlet 110, circulated through the conduit 106 and passed out the fluid outlet 112. The circulation of the thermally transmissive fluid through the conduit 106 thereby affects the temperature of the conduit 106 which is configured to affect the temperature of a tissue. The thermally transmissive fluid can be supplied to the surface area expansion element 62 via a circulation member as shown and described herein.

In operation, the surface area expansion element 62 can be inserted into an opening in a body by placing the distal end 114 into the opening and "screwing" the rest of the conduit 106 into the opening. This arrangement allows the surface area expansion element 62 to have a greater diameter than the opening into which it is inserted. For example, the surface area expansion element 62 has a diameter $d_s$ measured from the widest points around a circumference which ranges from approximately 10 mm to approximately 80 mm. In one embodiment the $d_s$ is approximately 60 mm. Additionally, the surface area expansion element 62 has a height $h_s$ measured from a top portion to a bottom portion which ranges from approximately 1 mm to approximately 10 mm. In one embodiment the $h_s$ is approximately 4 mm to 5 mm.

In an alternate operation, the expansion element 62 can be inserted into the skull in a contracted or deflated state and once placed into position, deployed or inflated with a thermally conductive fluid at a flow rate and fluid pressure.

Figure 15:
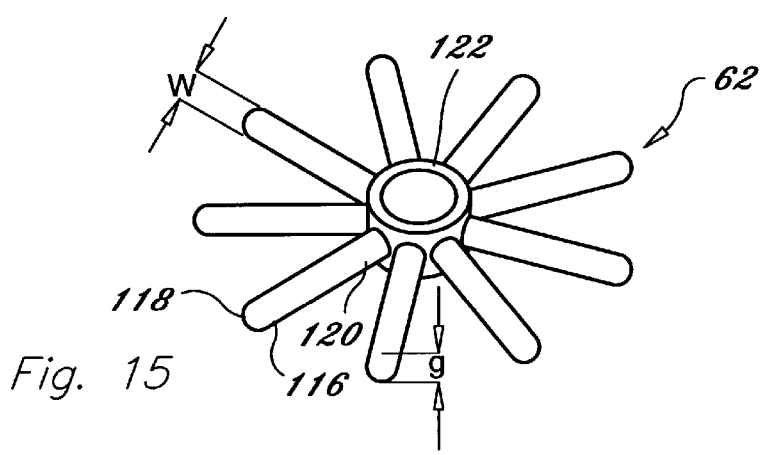
FIG. 15 is a perspective view of another exemplary surface area expansion element.

FIG. 15 is a perspective view of another alternate surface area expansion element 62 as shown in FIGS. 8, 9 and 10. The surface area expansion element 62 has at least one element arm 116 which has a distal end 118 and a proximal end 120 opposite the distal end 118, in which each element arm 116 is joined at the proximal end 120 to a port 122 to create a "spider-like" surface area expansion element arrangement. Each element arm 116 has a height g measured from a top of the element arm 116 to a bottom of the element arm 116. Further, each element arm 116 has a width w measured from a first side of the element arm 116 to a second side of the element arm 116. Further, each element arm 116 preferable has approximately a 2 to 1 width w to height g ratio. Additionally, a supply of thermally transmissive fluid to the surface area expansion element 62 can be provided in accordance with the invention herein.

The materials used to construct the surface area expansion element 62 described herein include one or more of compliant, non-compliant, and partially compliant polymers.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A device for thermally affecting tissue, comprising:
   a contact member, the contact member being thermally transmissive;
   a thermal member having a thermal input side and a thermal output side, the thermal input side being in thermal communication with the contact member;
   a first thermal fluid circulation member, the a first thermal fluid circulation member provided to circulate thermal fluid across the thermal output side of the thermal member;
   a housing, the housing having an interior surface for mounting the contact member, the first thermal member and the thermal fluid circulation member and the housing being configured to fit within a burr hole in a skull; and
   a surface area expansion element, the surface area expansion element, having an interior volume filled with a thermally-transmissive fluid, the thermally-transmissive fluid being in thermal communication with the contact member.

2. The device according to claim 1, wherein the surface area expansion element has a spiral shape.

3. The device according to claim 1, wherein the surface area expansion element has a spider-like shape.

4. The device according to claim 2, wherein the surface area expansion element, has a width measured at a widest part of the outside periphery of the spiral and a height measured from a top to a tissue contact surface area, the width being at least twice the height.

5. The device according to claim 4, further comprising a fluid circulation circuit including a second circulation member and at least one injection member.

6. The device according to claim 5, wherein the second circulation member is a pump.

7. The device according to claim 5, wherein the contact member defines an access port.

8. The device according to claim 7, wherein the access port contains a pressure sensor.

9. The device according to claim 7, wherein the access port contains a temperature sensor, the temperature sensor being configured to detect the temperature of a tissue to be treated.

10. The device according to claim 1, wherein the thermal member removes heat energy from the contact member via the thermal input side and radiates heat energy via the thermal output side.

11. The device according to claim 1, wherein the thermal member is a thermocooler.

12. The device according to claim 1, further comprising a thermal sink, the thermal sink being in thermal communication with the thermal output side of the thermal member and being operable to radiate heat energy.

13. The device according to claim 1, wherein the first thermal fluid circulation member is a fan and the thermal fluid is air, wherein the fan circulates air across a thermal sink to dissipate heat energy.

14. The device according to claim 1, wherein the first thermal fluid circulation member is a pump and the thermal fluid is a liquid.

15. The device of claim 1, wherein the housing is substantially cylindrical in shape.

16. The device according to claim 15, wherein a portion of the cylindrical shape of the housing is threaded.

17. A device for thermally affecting tissue, comprising:

a thermal cartridge having:
   a contact member, the contact member being thermally transmissive;
   a thermal member having a thermal input side and a thermal output side, the thermal input side being in thermal communication with the contact member;
   a thermal fluid circulation member, the thermal fluid circulation member provided to circulate thermal fluid across the thermal output side of the thermal member;

to a housing, the housing having an interior surface for mounting the contact member, the thermal member and the thermal fluid circulation member and the housing being configured to fit within a burr hole in a skull; and a surface area expansion element, the surface area expansion element, having an interior volume filled with a thermally-transmissive fluid, the thermally-transmissive fluid being in thermal communication with the contact member.

* * * * *